United States Patent [19]
Beal et al.

[11] Patent Number: 4,645,486
[45] Date of Patent: Feb. 24, 1987

[54] DEVICE FOR DRAWING AND PROCESSING BLOOD AND FOR ADMINISTERING LIQUID VIA PARENTERAL INJECTION

[75] Inventors: Charles B. Beal, Menlo Park; C. Bruce Fields, Pittsburg; David L. Stewart, Montara, all of Calif.

[73] Assignee: International Health Services, East Palo Alto, Calif.

[21] Appl. No.: 619,492

[22] Filed: Jun. 11, 1984

[51] Int. Cl.$^4$ .............................................. A61N 1/00
[52] U.S. Cl. ........................................ 604/4; 604/37; 604/132; 604/133; 604/185; 604/214; 604/316; 604/403; 604/411
[58] Field of Search ................. 604/4, 5, 6, 37, 52, 604/90, 91, 132, 133, 153, 181, 185, 212, 214, 313–319, 403, 408, 410, 411, 414; 128/DIG. 26

[56] References Cited

U.S. PATENT DOCUMENTS

| | | | |
|---|---|---|---|
| 1,676,881 | 7/1928 | Anthony | 604/212 |
| 2,771,879 | 11/1956 | Salisbury, Jr. | 604/214 |
| 2,862,496 | 12/1958 | Hassler et al. | 604/212 |
| 3,089,489 | 5/1963 | Dunmire | 604/212 |
| 3,099,264 | 7/1963 | Hubbard | 604/214 |
| 3,572,340 | 3/1971 | Lloyd et al. | 604/133 |
| 3,640,275 | 2/1972 | Burke et al. | 604/177 |
| 3,722,508 | 3/1973 | Roberts | 128/DIG. 26 |
| 4,201,207 | 5/1980 | Buckles et al. | 604/132 |
| 4,284,209 | 8/1981 | Barbour, Jr. | 604/403 |
| 4,410,323 | 10/1983 | Hodosh et al. | 604/212 |
| 4,425,114 | 1/1984 | Schoendorfer et al. | 604/7 |
| 4,473,369 | 9/1984 | Lueders et al. | 604/283 |
| 4,475,906 | 10/1984 | Holzner | 604/212 |
| 4,504,267 | 3/1985 | Parmelee et al. | 604/134 |
| 4,525,166 | 6/1985 | Leclerc | 604/30 |
| 4,559,035 | 12/1985 | Benjamin et al. | 604/133 |
| 4,581,021 | 4/1986 | Landau et al. | 604/214 |
| 4,583,972 | 4/1986 | Hunter, III et al. | 604/133 |

FOREIGN PATENT DOCUMENTS

| | | | |
|---|---|---|---|
| 799218 | 11/1968 | Canada | 604/240 |
| 1076899 | 3/1960 | Fed. Rep. of Germany | 604/212 |
| 1316596 | 12/1962 | France | 604/212 |
| 1454540 | 11/1976 | United Kingdom | 604/240 |

*Primary Examiner*—Stephen C. Pellegrino
*Assistant Examiner*—Mark Rooney
*Attorney, Agent, or Firm*—Iver P. Cooper

[57] ABSTRACT

This invention relates to a "plungerless" means of drawing blood and for administering liquids via parenteral injection. This means is used in conjunction with a pouch bearing an injection means, to which it is releasably attached. It comprises hinged plates which, when folded, expand the pouch; and which, when straightened, compress it.

In a preferred embodiment, the plates fold along a line essentially parallel to the general direction of fluid flow, and extend beyond the distal end of the pouch. The expanded pouch may then be rested on the distal edges of the plates, which form a "diamond" configuration.

6 Claims, 35 Drawing Figures

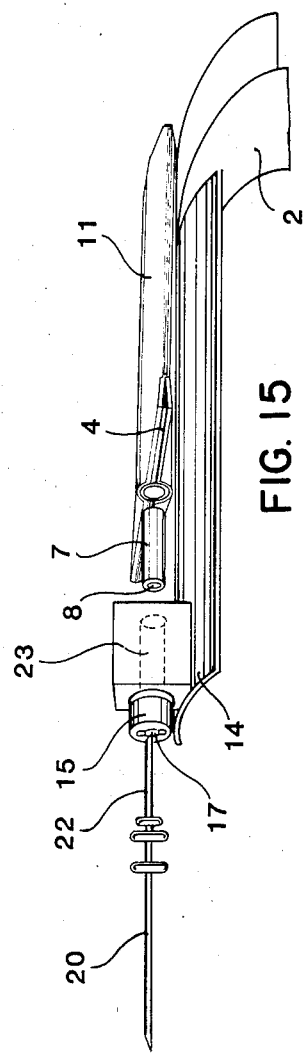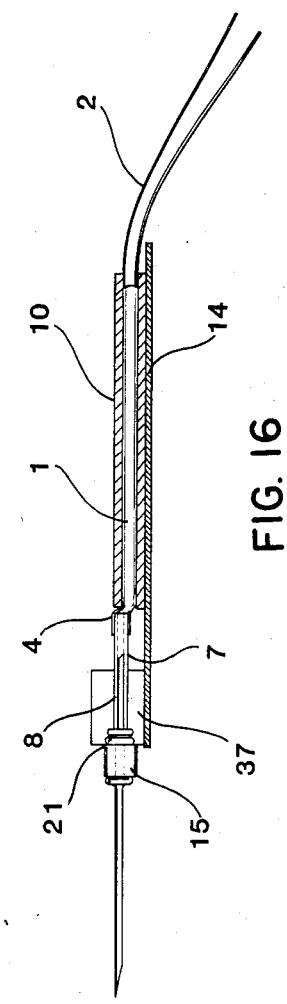

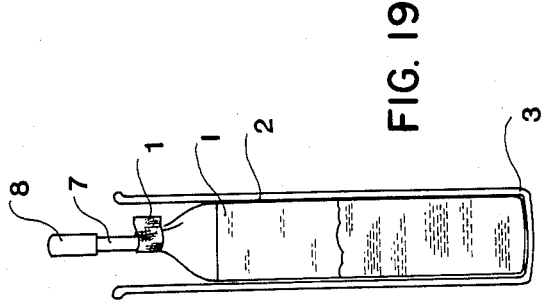
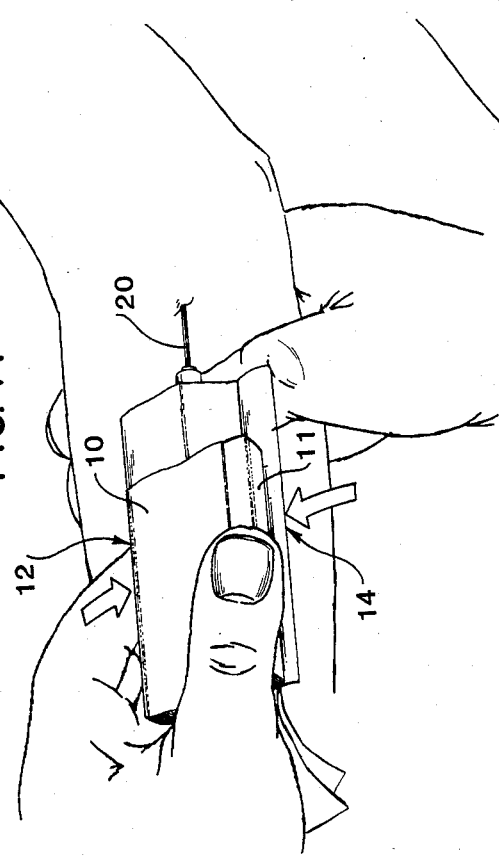
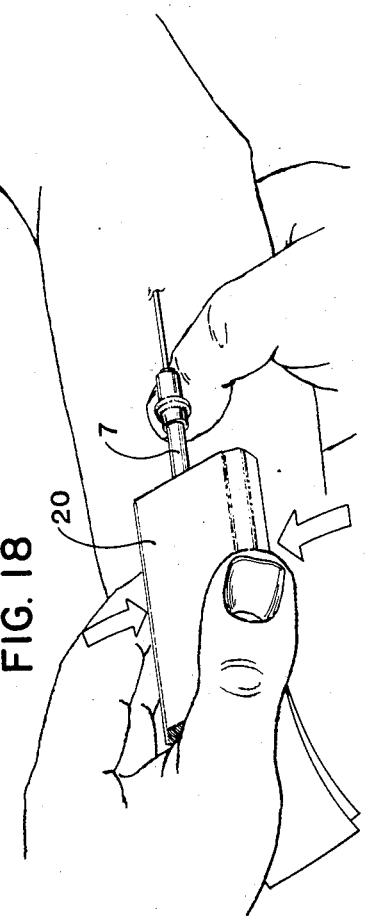

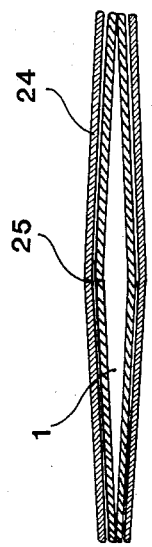
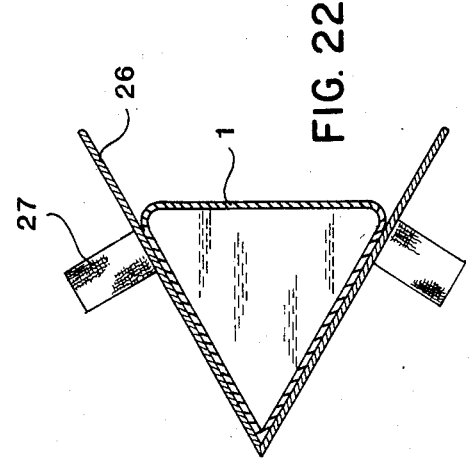
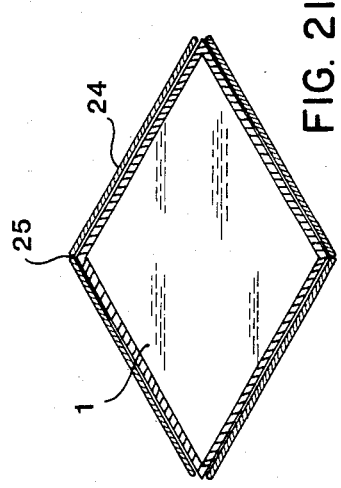
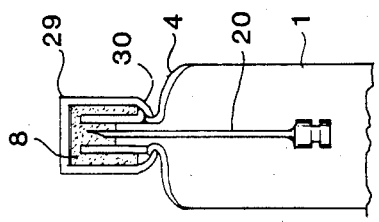
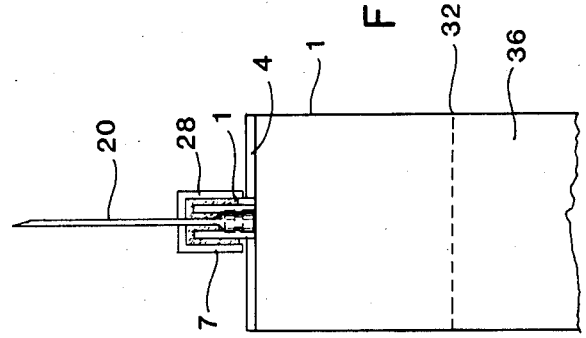

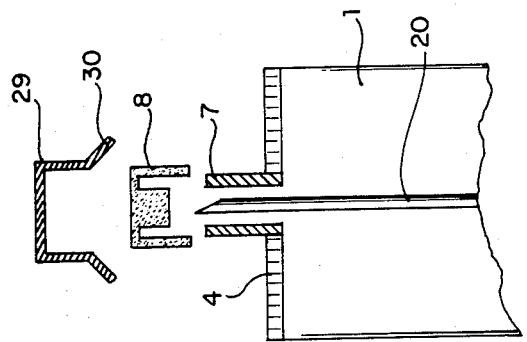
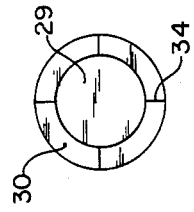
FIG. 24
FIG. 25
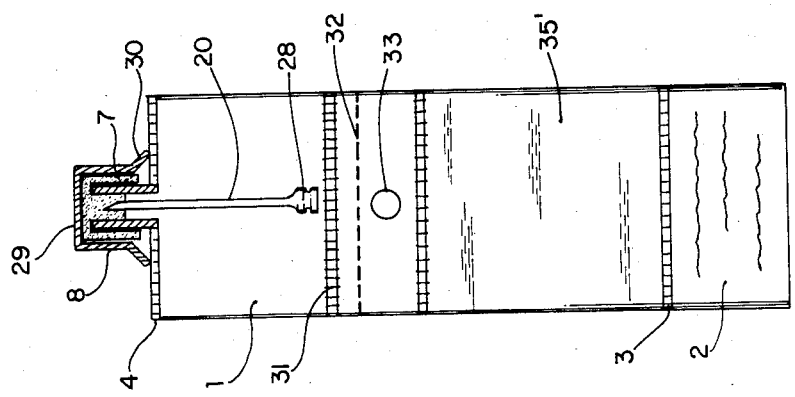
FIG. 23
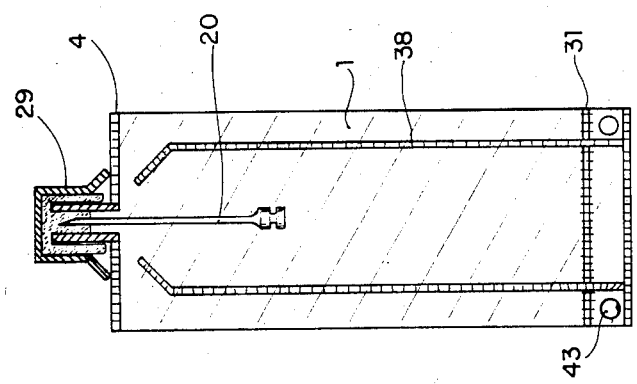
FIG. 29

DEVICE FOR DRAWING AND PROCESSING BLOOD AND FOR ADMINISTERING LIQUID VIA PARENTERAL INJECTION

BACKGROUND OF THE INVENTION

This invention relates to "plungerless" devices for drawing blood and for administering liquids via parenteral injection. In the devices of this invention, the volume of the collection or medication chamber is increased, and negative pressure thereby created, through the action of hinge means connecting rigid plates at least one of which is in continued contact with the exterior sides of the chamber. Different embodiments are described in which the device employs either a separable or integral means for altering the volume of the chamber and thereby causing flow into or out of the chamber.

"Plunger"-type syringes for the collection of arterial or venous blood, or for the parenteral injection of substances, are well known. Tolerances for these plungers are such that it is difficult to achieve consistently a fit that is neither too snug nor too loose. They are too bulky to be inserted at a shallow angle into a blood vessel. They roll easily and are often fragile. Two hands are necessary to create negative pressure within them (one to withdraw the plunger and the other to hold the housing). They do not have components that are reusable without resterilization. Other disadvantages of these syringes are well known to medical practitioners.

Devices which have inherent negative pressure may cause damage to blood cells and to blood vessels, and also have a limited shelf life. They, too, are bulky and difficult to manipulate.

Villari, U.S. Pat. No. 4,187,860 shows a "plungerless" arterial blood collector. It is a passive system designed to exert a minimum of pressure on the collection bag. It cannot be used to draw venous blood and cannot easily be filled completely with arterial blood (i.e., air would not be excluded). In addition, so that his back plate does not interfere with the filling of the bag, his needle adapter must be offset from the back plate. Consequently, the needle of the Villari device cannot be inserted at as small an angle of entry as made possible by the present device.

In the "bellows"-type syringes previously known, Krasno, U.S. Pat. No. 2,717,598, Bane, U.S. Pat. No. 3,340,869, and van Leer, U.S. Pat. No. 3,991,757, measurement of the volume of blood received would be difficult. Neither do they lend themselves to "shallow" injection. There is also a danger of injecting air into the patient.

In the simplest "plungerless" syringes such as Lockhart, U.S. Pat. No. 2,727,516, Gerarde, U.S. Pat. No. 2,907,326, and Pogorski, U.S. Pat. No. 3,662,928 air cannot easily be completely expelled, and one might inadvertently inject air into a patient during phlebotomy.

SUMMARY OF THE INVENTION

This invention employs hinged plate means permanently or temporarily bonded to a collection pouch to force apart the sides of the pouch, thus creating negative pressure within.

One object of the invention is to provide a device for drawing blood by creating negative pressure within the device without recourse to syringe barrels and plungers, or the inherent elasticity of a bellows or a concertina mechanism.

Another object of the invention is to maintain operator control over the negative pressure obtained, and hence the rate of blood flow.

Another object of the invention is to make it less likely that the drawing of blood will cause the collapse of the vein or cell damage.

Another object of the invention is to provide a device for drawing blood having unlimited shelf life.

Another object of the invention is to permit phlebotomy to be conducted with the needle inserted into the vein at a shallow angle, i.e., one nearly parallel to the long axis of the vein.

Another object of the invention is to provide a device for drawing blood, which can be dropped without breaking, which will not roll off a table, and in which in general can survive rough usage.

Another object of the invention is to provide a device for drawing blood in which the components coming in contact with the blood are inexpensive, compact, sterilizable and disposable.

Another object of the invention is to provide a device for drawing blood in which the components not coming in contact with the blood are inexpensive, simple to use, and reusable.

Another object of the invention is to provide a device for drawing blood in which the pouch for holding the blood may be readily replaced, thus permitting several pouches to be filled sequentially.

Another object of the invention is to provide a device in which the pouch is stably held in place by opposing forces.

Another object of the invention is to provide a device with a needle means in which the needle can be locked into place with but a modest rotation of the shaft.

Another object of the invention is to provide a device for drawing blood with an integral needle means whereby the needle cannot fall off or be misplaced and where potentially contaminating manipulations of the needle for use are unnecessary.

Another object of the invention is to provide a device for drawing blood whose needle may be safely disposed of without actual removal or hazard of injury from the needle point.

Another object of the invention is to prevent interference by extraneous oxygen or carbon dioxide in the course of measurements of blood gas volumes.

Another object of the invention is to permit blood to be sequestered in separate compartments for individual handling.

Another object of the invention is to provide a device for drawing blood which may also be used for administering liquids by parenteral injection.

Another object of the invention is to permit an operator to determine whether a blood vessel has been entered, and to do so one-handed.

Another object of the invention is to provide filtering means to prevent large undissolved particles from being injected.

BRIEF DESCRIPTION OF THE DRAWINGS

The device in its preferred embodiment is best understood by referring to the illustrations, of which.

Figure 9:
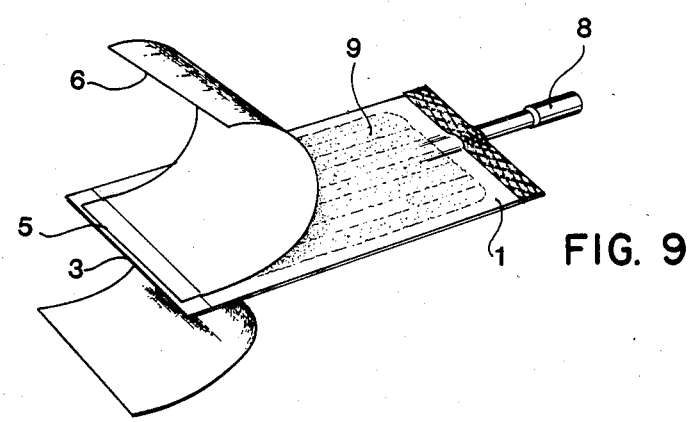
Figure 10:
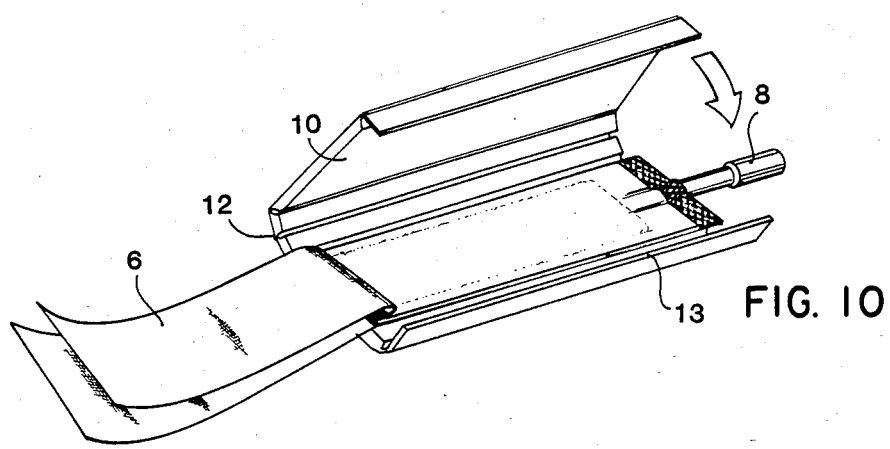
Figure 11:
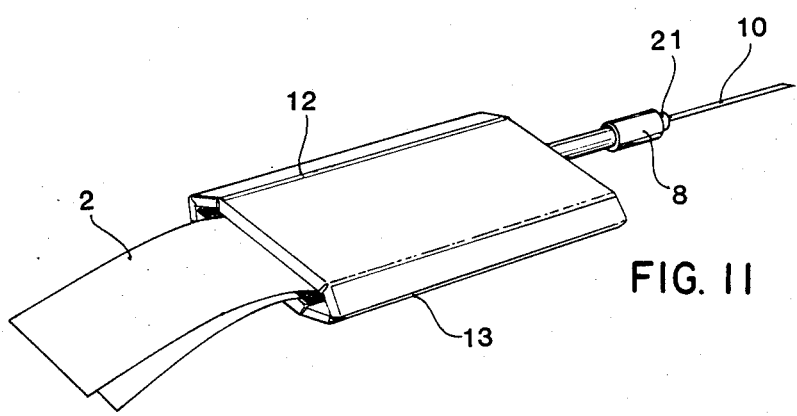

(b) is a view from behind;

FIGS. 9 to 11 show the manner of use in which the pouch assembly is placed in the squeeze box. In FIG. 9 both labels are peeled away from the surface of the pouch. In FIG. 10 the pouch is placed in the squeeze box, and in FIG. 11, the squeeze box is closed.

Figure 12:
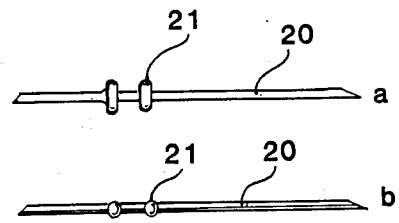
Figure 13:
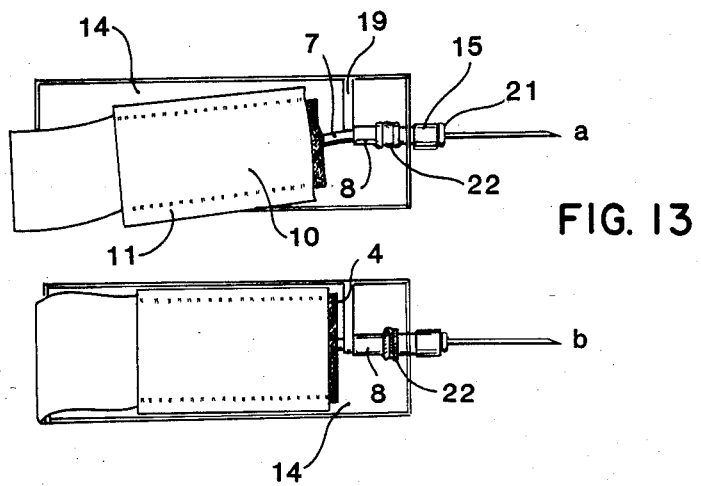

FIG. 12 (a) is a top view of the needle;

(b) is a side view of the needle;

FIG. 13 (a) shows a pouch assembly contained within a squeeze box being placed in the needle holder (which is of slightly different configuration from that of FIGS. 5-8);

(b) shows the pouch assembly fully placed within the needle holder.

Figure 14A:
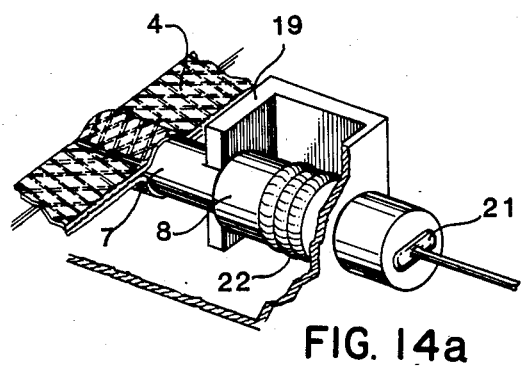
Figure 14B:
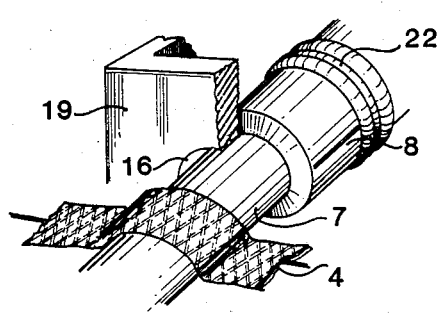

FIG. 14 (a) and (b) show the method by which the pouch assembly locks into the needle holder.

FIG. 15 shows a needle holder of yet another design, with both the needle and pouch assembly in position to be engaged into the needle holder.

FIG. 16 is a schematic longitudinal section of the pouch assembly within the squeeze box and engaged in the needle holder. The needle also is engaged in the holder.

FIG. 17 shows the method of use of the fully assembled device in which phlebotomy is being accomplished.

FIG. 18 shows the same method of use but without utilizing the needle holder.

FIG. 19 shows schematically the pouch containing blood and placed within a centrifige tube container.

FIG. 20 shows a cross-section of a modification of the device in which two longitudinally scored flexion plates are attached to the pouch, eliminating the need for a squeeze box.

FIG. 21 shows the variation of FIG. 20 filled with blood.

FIG. 22 shows a cross section of another modification in which two extension plates with finger grips are attached to the pouch.

FIG. 23 shows a schematic top view of a modification of the pouch in which the hypodermic needle is inherently contained within the pouch and in which seals are placed in such a manner as to contain liquid and dry components of an injectable substance.

FIG. 24 is a schematic expanded and enlarged view of the upper portion of the device of FIG. 23.

FIG. 25 is a top view of the rigid cap of FIG. 24.

FIG. 26 is a schematic view of the device being made ready for use by extending the needle and rupturing the frangible seals.

Figure 28:
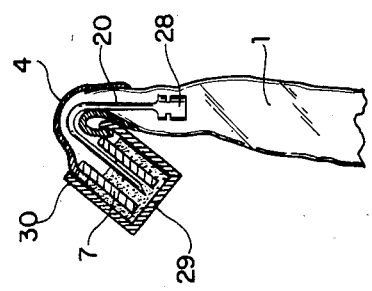

FIGS. 27 and 28 are schematic views of the retraction and securing of the needle after use.

FIG. 29 is a view of a modification in which the pouch is constructed containing six compartments.

Figure 30:
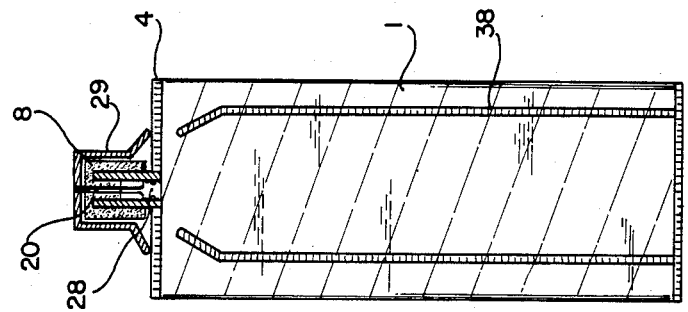

FIG. 30 shows the modification of FIG. 29 during use after phlebotomy has been accomplished.

Figure 32:
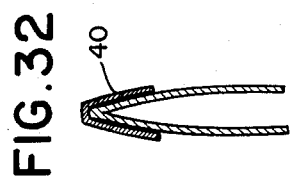
Figure 31:
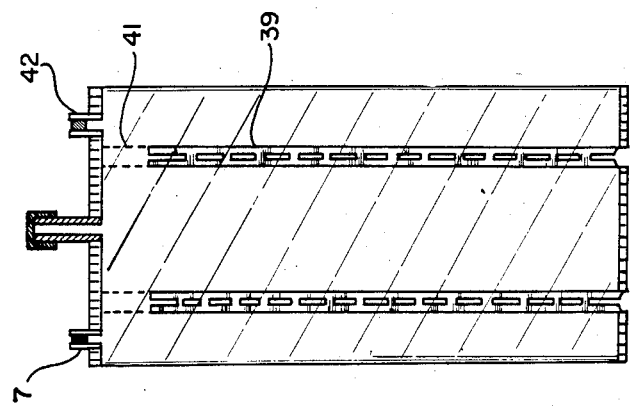

FIG. 31 shows a front view of another modification, of which a sagittal section appears in FIG. 32.

Figure 33:
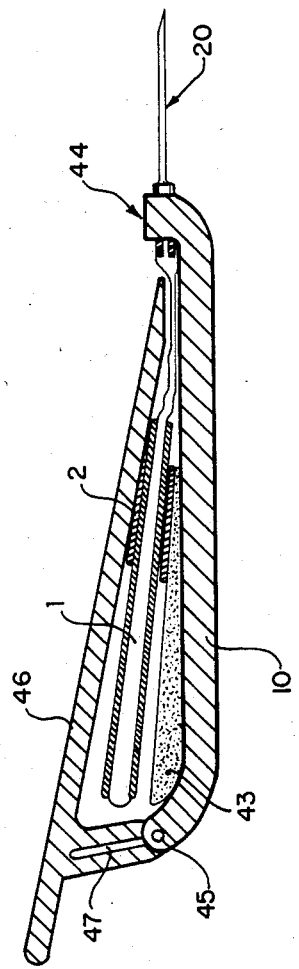

FIG. 33 shows a profile view of yet another modification.

DETAILED DESCRIPTION OF THE INVENTION

The device in its preferred configuration is an integrated four component system:

(A) pouch assembly
(B) squeeze box
(C) needle holder
(D) hypodermic needle (A) The pouch assembly (FIGS. 1-3) is a flexible, transparent pouch (1) constructed preferably of 0.005 inch thick polyvinyl chloride film which is of medical grade and radiation resistant. A rectangular unexpanded shape offers manufacturing convenience, but other shapes are employable and may offer advantages in use. The width of the pouch is approximately ⅞ inch and the length 3½ inches. On either side of the pouch is a paper label (2) attached to the pouch in a nonpermanent fashion by an adhesive (9). The lower end of the label (5) on each side is permanently fixed to the lower seal of the pouch (3). Within the upper seal of the pouch (4) is fixed a transparent, rigid tube, the neck (7), on the distal end of which is placed a rubber cap (8).

Figure 4:
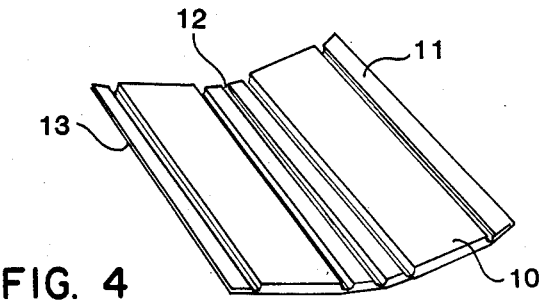
FIG. 4 is a view of an opened squeeze box.
Figure 5:
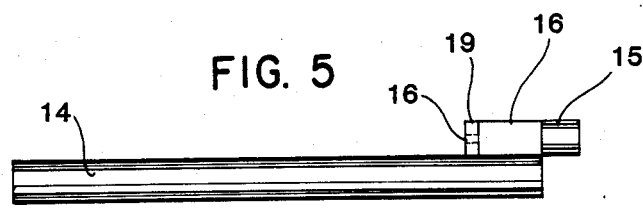
FIG. 5 is a schematic side view of the needle holder.
Figure 6:
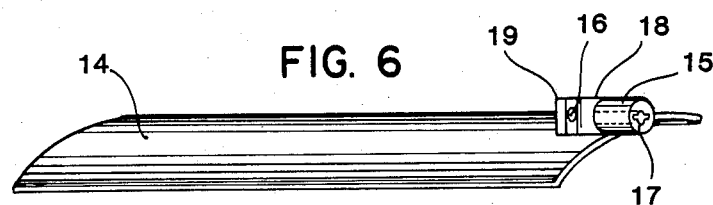
FIG. 6 is a view of the needle holder in perspective.

(B) The squeeze box (FIG. 4) consists of two equal halves attached by a hinge (12). Each half contains a thick, transparent, rigid adhesion plate (10) ⅞ inch wide and 3½ inches long. A thin walled, narrow flexion plate (11) is attached by a hinge on either side of the adhesion plate. Thus, on each half of the device one of the flexion plates contains a free edge (13).

(C) The needle holder (FIGS. 5-8) consists of an elongated arm plate (14) slightly convex in its narrower dimension. Protruding beyond one end of the arm plate is a cylindrical needle adapter (15) containing a laterally notched needle entry (17) traversing the length of the cylinder. Attached to the left side of the cylinder (as viewed from behind) is the side plate (18), which is attached at a right angle to the back plate (19). The free vertical edge of the back plate contains a semi cylindrical notch (16).

The distance between the needle adapter and the back plate is approximately ⅛" longer than the rubber cap of the pouch assembly. The diameter of the notch is 1/32" larger than the diameter of the neck of the pouch assembly.

(D) The hypodermic needle (FIG. 12) consists of a pointed hollow shaft (20) and a needle flange (21) attached to the external surface of the shaft approximately 1" from the end of the needle opposite the point. A second flange is placed approximately ¼" proximal to the first. The distance between the two flanges is equal to the length of the needle adapter on the needle holder. A rubber shield (22) (FIG. 15) may be used to cover the lower end of the needle.

Figure 7:
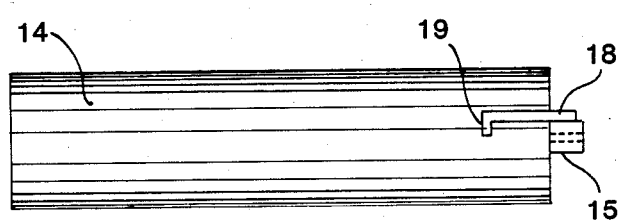
FIG. 7 is a top view of the needle holder.
Figure 8A:
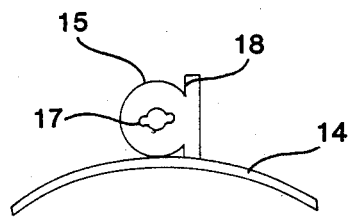
FIG. 8 (a) is a front view of the needle holder.
Figure 8B:
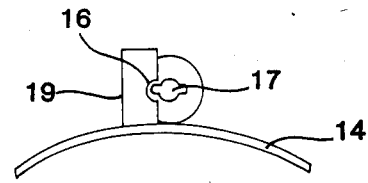

A modification of the device is shown in FIG. 13 in which the side plate of FIG. 7 is omitted. Another modification is shown in FIGS. 15-17 in which a transparent block (37) replaces the side and back plates. Within the block is a horn-shaped channel of a size to fit snugly the rubber cap of the pouch assembly. In this modification, friction between the cap and the sides of the channel prevents any inadvertent change in the relative positions of the needle and the pouch assembly.

A modification of the pouch assembly is pictured in FIG. 20 in which a cross-section shows the addition to either side of the pouch a flexion plate (24) with a longitudinal score (25) in its center line.

Another modification is pictured in FIG. 22 in which an extension plate (26) is attached to a portion of each side of the pouch. Each extension plate has an attached finger loop (27).

Figure 1:
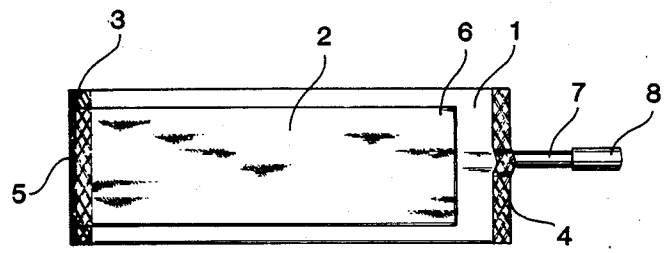
FIG. 1 is a top view of the pouch assembly.
Figure 2:
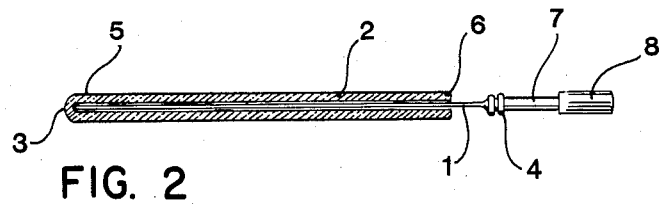
FIG. 2 is a schematic longitudinal section of the pouch assembly.
Figure 3:
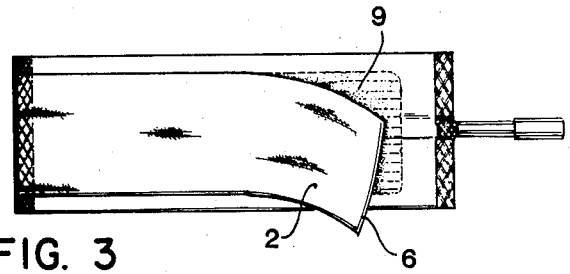
FIG. 3 is a top view showing a label partially peeled back.

Other modifications of the pouch assembly and hypodermic needle are shown in FIGS. 23-27. The hypodermic needle of FIG. 12 is replaced by a needle containing a cylindrical hub (28). The rubber cap is covered with a rigid cap (29). The lower portion of the cap is expanded to become a flared rim (30) containing four equidistantly spaced deep cuts, the rim scores (34). In this modification the internal diameter of the neck (7) is such that it is able to admit snugly the hub of the hypodermic needle. Just below the needle hub the two faces of the pouch are non-permanently adhered with a transverse frangible seal (31). Just below this frangible seal the two faces are permanently adhered with an interrupted filtering seal (32). Beneath this seal, and above a second frangible seal is a wafer of biologically active material in dry form, the dry component (33). Below the second frangible seal is contained the liquid component (35) of the contents within the pouch. Not shown in the figures are the labels and adhesive which are of the same general configuration as in the preferred embodiment (FIGS. 1-3).

In another modification (FIG. 29) a permanent vertical seal (38) near one edge of the pouch, and another near the opposite edge form three chambers. The vertical seals are angled slightly inwards near their upper ends. A non-permanent frangible seal near the bottom of the pouch subdivides the chambers to form a total of six compartments. The three lower compartments may contain biologically active agents, such as an anticoagulant (43).

To perform phlebotomy, all four interacting components of the system are used. First, the pouch is readied (FIG. 9) by peeling back the two labels, exposing the adhesive. Next the pouch is placed within the squeeze box (FIG. 10), and the box closed (FIG. 11), exerting some finger pressure on the top of the box to assure adherence of the adhesive to the adhesion plates. Next, the hypodermic needle is inserted into the needle adapter, the lower flange passing through the laterally notched needle entry. The needle then may be turned slightly to lock it in place. The pouch assembly contained within the squeeze box is pushed into place (FIGS. 13, 14), the lower end of the needle penetrating the rubber cap and passing into the neck. This action causes the end of the rubber shield to be pushed forward on the needle in concertina fashion. When the neck of the pouch is fitted into the notch of the needle holder, the lower portion of the rubber cap engages the front of the back plate. The rubber shield exerts counter pressure, holding the pouch assembly in place during phlebotomy. The vein then is entered by percutaneous needle puncture. To create negative pressure within the pouch, the flexion plates of the squeeze box are pressed inward (FIG. 17). This action begins to force apart the adhesion plates, and with them the attached sides of the pouch. The transparent pouch and squeeze box allows the operator to visualize the quantity of blood within the pouch. When sufficient blood has been obtained, or the pouch is full, the squeeze box and contained pouch assembly are removed from the needle and needle holder. If an additional quantity of blood is to be drawn, the needle remains in place and a second pouch in its squeeze box is engaged, and the phlebotomy process continued. This procedure may be repeated several times if necessary. Next, the needle holder and needle are withdrawn from the vein.

If only one pouch of blood is needed, then the needle holder need not be used, and instead an hypodermic needle of the present invention, or a standard single specimen needle, may be inserted directly into the rubber cap (FIG. 18). Phlebotomy then proceeds as described above. The portion of the label containing space for the phlebotomized person's name or other identification may be filled out at this time, or prior to the actual phlebotomy process. The pouch then is pulled away from the squeeze box as the latter is opened, and the labels replaced onto the adhesive. If it is desired to separate the blood into its liquid and solid components within the pouch, the pouch may be placed in a standard centrifuge tube holder (FIG. 19) and centrifugation performed. The pouch is removed from the holder, its rubber cap removed, and the liquid component (serum or plasma) poured off. The cap then may be replaced. If desired, a clip or a permanent heat induced seal may be placed across the pouch to more securely separate the components before pouring off the liquid.

Several modifications are illustrated and have been described. The modification of the needle holder as seen in FIGS. 15-17 depends upon a snug friction fit to maintain the pouch assembly in place during phlebotomy.

The modification of the pouch assembly as seen in FIG. 20 eliminates the need for a squeeze box. Lateral pressure on the device tends to separate the faces of the pouch, creating negative pressure and allowing blood to enter (FIG. 21).

In the modification of FIG. 22 negative pressure is achieved by placing the fingers in the finger loops and pulling the extension plates apart.

In the modifications of FIGS. 23-27 the primary purpose is not phlebotomy, but rather parenteral injection of a biologically active substance, for example an antibiotic. The dry and liquid components segregated within the pouch are mixed prior to injection by rupturing the lower frangible seal through external pressure on the liquid-containing portion of the pouch. By external manipulation of the pouch, the needle may be forced through the rubber cap and fully extended until the hub is tightly engaged in the neck of the pouch. The pouch then may be placed in the squeeze box as described (FIGS. 9-11). If intravenous injection is intended, the needle is inserted into a vein.

To verify proper intravenous needle placement, the squeeze box is used to create slight negative pressure allowing blood to enter the pouch. If subcutaneous or intramuscular injection is intended, the same production of negative pressure can help to insure that the needle has not entered a vein in that no blood enters the pouch. Pressure on the adhesion plates increases fluid pressure, rupturing the upper frangible seal and forcing the liquid through the needle. Any undissolved particles are trapped by the filtering seal, and are not injected. After injection is accomplished, the needle may be disposed of by cutting off the shaft at the surface of the rubber cap and replacing the rigid cap, or the rigid cap may be used to force the needle shaft back into the pouch. The flared rim of the rigid cap helps to protect the fingers of the operator from accidental injury from the needle point. When the rigid cap is fully in place over the rubber cap, downward pressure on the rim breaks the rim into four sections by tearing the rim at its weak points, the rim scores. The rim sections then may be bent under the neck (FIG. 27), securing the rigid cap from coming off of the device. If further anchoring of the needle is desired, then the needle hub may be held through the plastic pouch while the rigid cap is sharply turned to one side (FIG. 28). This action bends the needle shaft. As the amount of bending of the shaft increases, the needle becomes increasingly difficult to dislodge.

The use of the modification for phlebotomy shown in FIG. 29 is similar to that of the preferred embodiment. After the blood is in the pouch, the shaft of the needle is cut off at the level of the rubber stopper, and the rigid cap replaced. The blood then may be distributed to the three vertical chambers by external manipulation as desired and a clip placed across the pouch at the level of the tops of the vertical seals, thus isolating the blood in each of these chambers. External pressure on each of these chambers causes the frangible seals to rupture. The anticoagulant (43) then can be mixed with the blood. Centrifugation allows for the separation of the liquid and solid components of the blood. By manipulation of one or more external clips near the top of the pouch, a part or all of the various contents can be poured off through the truncated needle. If desired, one or more chambers may be emptied prior to centrifugation.

The system and devices of the preferred embodiment may be additionally modified as follows: the pouch may be of variable dimensions. The plastic film may be made of various polymers, copolymers or laminates. Film thickness also may vary. The pouch may contain a plurality of compartments with vertical, horizontal, oblique and interrupted seals. The seals may be permanent or frangible. Various materials may be included in the pouch and may be sequestered in one of the compartments of the pouch. Such materials include anticoagulants and gels to help separate the liquid and cellular components of blood. Or they may include injectable agents such as antibiotics and vaccines.

The squeeze box, arm plate and hypodermic needle may be of various sizes and shapes and constructed of various materials. The lower flange on the needle may be eliminated entirely. A small protuberance may be substituted for the lower flange. The flanges may also be replaced by discs co-concentric with the shaft. The discs may be of a diameter to fit snugly into the neck of the modification as depicted in FIGS. 23, 24, and 26. The needle may be constructed of metal or of hard plastic material. The manner in which the hypodermic needle is incorporated into the modifications of FIGS. 23, 24 and 26 for parenteral injection may also be used for phlebotomy. In such a case the needle holder is not used.

The phlebotomy pouch may be manufactured containing within it a small quantity of nitrogen or other physiologically inert gas. This modification may be applicable to arterial blood drawing for blood gas determination. The gas would be expressed just prior to percutaneous puncture, thus eliminating all oxygen and carbon dioxide from the system.

A schematic front view of another modification is shown in FIG. 31 in which the vertical seal (39) is widened and multiply slotted along its center line. There is a shortened neck (7) directly above each lateral compartment. A rubber plug (42) occludes the upper part of the lumen of each neck. Markings (41) extending from each vertical seal upwards to the upper seal of the pouch to indicate the area for heat sealing during use. Additional lateral chambers may be included in the device.

The manner of use of this modification allows for filling using the squeeze box, as previously described. By external manipulation, blood or other fluid is made to enter the lateral chambers. An impulse type heat sealer then is used to seal the leaves of the pouch together above the vertical seals in the areas encompassed by the dotted lines. The two lateral chambers then may be torn away from the central chamber, and the heat sealed areas cut along their center lines. This action produces three separate containers of blood from a single device and a single phlebotomy. At a later time the contents of the lateral compartments can be removed by hypodermic needle in puncturing the rubber plugs.

A schematic sagittal section of the upper portion of a lateral chamber is shown in FIG. 32. This is a modification of the device of FIG. 31. In this modification the neck and rubber plug are substituted for by an adhesive rubber membrane (40). This membrane may be placed on the lateral chamber at the time of manufacture, or at the time of use. To withdraw fluid from the chamber an hypodermic needle is used simply to pierce one leaf of the pouch through the rubber membrane.

The advantage of the modification of FIG. 31 is that three or more separate blood samples may be produced from a single device. These samples may be distributed to different areas in a laboratory, or some of the samples may be stored for future use. The impulse heat sealer also may be used to seal the compartments transversely after centrifugation, thus permanently separating the serum or plasma layer from the cellular layer.

The advantage of the modification of FIG. 32 is that of simplicity, and thus economy, of manufacture. Further, if the rubber membrane is not applied prior to use and the sample is stored for possible future use, the membrane need only be applied if the sample is to be withdrawn from the compartment.

The advantages of the devices and system of the present invention over other known devices for drawing and processing blood and parenteral injection are numerous.

Negative pressure within the device may be obtained without recourse to syringe barrels and plungers, or the inherent elasticity of a bellows or a concertina mechanism.

There are several advantages over devices which have an inherent negative pressure (such as the Vacutainer ® tube).

In these devices there is no operator control of rate of blood flow or degree of negative pressure obtained. In the case of veins that easily collapse, high negative pressure may well collapse the vein against the needle opening, thereby obstructing flow.

Rapid blood flow that occurs when high negative pressure is present may well damage blood cells, causing some hemolysis, and interfering with certain blood tests. In the device of the present invention, careful control of negative pressure is possible, thus avoiding both collapse of veins and cell damage.

These devices also tend to lose their negative pressure over time, thus limiting shelf-life. The device of the present invention has unlimited shelf-life.

The pouch when filled with blood, can be dropped without breakage and can, in general, be handled more roughly than glass phlebotomy and centrifuge tubes without damage or loss of the blood. The pouch will not roll off of a table, as is the tendency with cylindrical tubes. The pouch is very inexpensive and compact, facilitating shipment and storage and eventual disposal. The pouch is presterilized and disposable. The squeeze box is inexpensive and simple to use. It can be used repeatedly.

The needle holder also offers several advantages. In the needle holder the closeness of the needle adapter to the arm plate permits the needle to be inserted into the vein at an angle nearly parallel to the long axis of the vein. This flat angle aids insertion and helps avoid penetration and damage to the opposite wall of the vein. With larger syringes and the Vacutainer R system the needle must be inserted at a more acute angle. The arm plate of the needle holder is slightly convex in shape to fit the contour of the donor's arm. The back plate and notch of the needle holder allows the pouch assembly to be rapidly and easily advanced on the needle and fixed in position for the manipulation of the squeeze box with one hand, leaving the other hand free to maintain the needle in its position in the vein. For this purpose the rubber shield on the needle when compressed serves to provide counter tension on the pouch assembly, providing additional stability. The pouches may be readily exchanged to allow filling of a plurality of pouches sequentially.

The hypodermic needle is simple in design and inexpensively manufactured. It interlocks with the needle adapter of the needle holder readily, and locks in place with only a quarter turn of the shaft. Currently used needles that fit into a commonly used needle holder (Vacutainer ® system) screw into place, requiring a few full rotations of the shaft.

In the modifications of FIGS. 20-22, the squeeze box is eliminated, thus avoiding one step in the phlebotomy process.

In the modifications whereby the system is used for parenteral injection the incorporation of the needle into the pouch has several advantages:

There is no risk of microbial contamination of the needle prior to use. With other currently used needles, this risk exists in the manipulation of the needle preparing it for use.

The needle will not fall off or be lost, as it is an integral part of the pouch assembly.

Safe disposal of the needle does not require it being cut off from the device or removed from the pouch and into another container.

The needle, when cut off can act as an egress channel for liquid within the pouch. The hazard from accidental injury from the needle point is eliminated. It is believed that a needle used in this manner is unique.

When used for arterial puncture to determine blood gas volumes, it is important to eliminate all extraneous sources of oxygen and carbon dioxide. This modification, along with the prior incorporation of pure nitrogen in the pouch, and using a plastic film or laminate virtually impervious to gasses, permit the easy performance of arterial puncture with virtually no risk of contamination with gas from an extraneous source.

The rigid cap and its rim cooperates to yield several advantages. The rim acts as a shield to protect the operator's fingers from accidental injury with the needle point. The cap itself is used to push the needle shaft back into the pouch. The rim, by virtue of its deep scoring, may be separated into four sections which can be bent under the neck of the pouch to secure the cap in place. The cap then may be grasped and flexed in relation to the needle shaft, thus bending the shaft. These actions secure the needle in place for a safe disposal.

In the modification of FIG. 23, the upper frangible seal serves to maintain the needle in its proper and safe position prior to use, while the lower frangible seal serves to separate liquid and dry components prior to use. This separation is useful when the dry component would have a reduced shelf-life when dissolved in the liquid. The filter seal of this modification prevents any large undissolved particles from being injected. This is advantageous for injections of particulate suspensions which may aggregate, or of solutions which may form precipitates when stored. The utilization of the squeeze box in conjunction with this modification permits the operator to create a slight negative pressure to determine whether a blood vessel has been entered. This action can be accomplished with one hand, whereas with a standard hypodermic syringe two hands generally are required to induce negative pressure.

A modification in which the phlebotomy device contains one or more vertical permanent seals has the advantage that a single pouch can serve the function of two or more pouches by sequestering blood in the separate compartments. By the additional use of external clips, the compartments can be emptied individually.

Another modification of the preferred embodiment pertains to the squeeze box when used for parenteral injection. The primary object of this modification is to apply pressure on the pouch first on the bottom and then progressively forwards.

The modification is shown in FIG. 33, which is a schematic profile view. The adhesive plate (10) is covered in its distal three quarters by a wedge shaped rubber cushion (43). Together they form a supporting means for the pouch. Rising from the front end of the plate are two projections forming a needle slot (44), the slot being of a width to hold snugly the hub of a hypodermic needle. Attached to the back end of the adhesive plate is an upward projection through which is placed a pin (45) to form a sliding hinge with pin slot (47) of a movable compression means, that articulate with the squeeze plate (46), which has a tapered undersurface at its front end. A downward projection near its back end containing elongated openings forming pin slot (47) allows for a hinging articulation with the adhesive plate with considerable vertical mobility.

The use of this modification is for intravenous, subcutaneous, or intramuscular injection from a pouch assembly containing an injectible liquid. The labels on either face of the pouch are peeled back about 2 cm. exposing adhesive coating on the pouch. The pouch then is placed on the adhesive plate, and the needle hub into the needle slot. The front part of the squeeze plate is brought into firm contact with the pouch. This action produces adherence of the upper part of both leaves of the pouch to the device. The front end of the squeeze plate then is elevated slightly separating the upper part of the leaves of the pouch and thus creating a negative pressure. This action permits the user to determine whether the needle has entered a vein. When the proper conditions are satisfied, the device is squeezed together, the heel of the hand applying the first pressure to make first contact with the lower end of the bag. Continuous squeezing then forces the liquid out of the pouch into and through the needle. The advantage of this modification is that it facilitates the ready and complete injection of liquids from the pouch assembly. The device also facilitates the preliminary obtaining of negative pressure within the pouch to verify the position of the needle point.

| Legend | |
|---|---|
| 1. pouch | 25. longitudinal score |
| 2. label | 26. extension plate |
| 3. lower seal of pouch | 27. finger loop |
| 4. upper seal of pouch | 28. hub |
| 5. lower end of label | 29. rigid cap |
| 6. upper end of label | 30. flared rim |
| 7. neck | 31. frangible seal |
| 8. rubber cap | 32. filtering seal |
| 9. adhesive | 33. dry component |
| 10. adhesive plate | 34. rim score |
| 11. flexion plate | 35. liquid component |
| 12. hinge | 36. mixed liquid and dry components |
| 13. free edge | |
| 14. arm plate | 37. block |
| 15. needle adapter | 38. vertical seal |
| 16. notch | 39. perforated vertical seal |
| 17. laterally notched needle entry | 40. adhesive rubber membrane |
| | 41. markings |
| 18. side plate | 42. rubber plug |
| 19. back plate | 43. rubber cushion |
| 20. needle shaft | 44. needle slot |
| 21. needle flange | 45. pin |
| 22. rubber shield | 46. squeeze plate |
| 23. channel | 47. pin slot |
| 24. flexion plate | |

We claim:

1. A separable device for altering the volume of a pouch means adapted for holding an injectable liquid, comprising hinged plate means, being adapted to be adhesively and releasably connected to said pouch means, said hinged plate means comprises, consecutively, a first flexion plate, a first adhesion plate flexibly connected to the first flexion plate, a second flexion plate fixedly connected to the first adhesion plate, a third flexion plate flexibly connected to the second flexion plate, a second adhesion plate flexibly connected to the third flexion plate, and a fourth flexion plate flexibly connected to the second adhesion plate, the first and fourth flexion plates each having a free edge, wherein the flexion plates are narrower and thinner than the adhesion plates, and the adhesion plates are adapted for adhesive connection to the pouch, whereby in a folded configuration said hinge plate means expands said pouch means, creating a partial vacuum therein, and in an unfolded configuration said hinged plate means compresses the pouch, expelling the liquid.

2. The device of claim 1, wherein the adhesion plates are transparent.

3. The device of claim 1, the hinged plate means having at least one inherent hinge in the form of a linear region of the plate means which is mechanically weaker than adjacent regions, whereby the plate means folds about the line defined by said linear region.

4. The device of claim 1, the hinge plate means comprising at least two plates flexibly connected by hinge means.

5. The device of claim 1, wherein the hinged plate means comprises an upper hinged plate means and a lower hinged plate means, each having at least two parallel edges, two parallel edges of said upper hinged plate means being flexibly connected to opposed edges of said lower hinged plate means, said hinged plate means each having at least one linear hinge region parallel to said connected edges, whereby inward pressure on said edges causes folding in said hinge regions.

6. The device of claim 5, wherein said hinged plate means are adapted to extend beyond the distal end of said pouch, each hinged plate means having a free distal edge, whereby the device, bearing said pouch, may stand upright on said distal edges when the hinged plate means are in the folded configuration.

* * * * *